United States Patent
Lee et al.

(10) Patent No.: US 12,178,942 B2
(45) Date of Patent: Dec. 31, 2024

(54) METHOD FOR MANUFACTURING STENT FOR DRUG RELEASE, INCLUDING FLEXIBLE NANOSTRUCTURED FILM CONNECTED IN THREE DIMENSIONS, AND STENT FOR DRUG RELEASE PREPARED THEREBY

(71) Applicant: KOREA INSTITUTE OF SCIENCE AND TECHNOLOGY, Seoul (KR)

(72) Inventors: Joonseok Lee, Seoul (KR); Eunyoung Jeon, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 803 days.

(21) Appl. No.: 17/336,321

(22) Filed: Jun. 2, 2021

(65) Prior Publication Data
US 2021/0393860 A1 Dec. 23, 2021

(30) Foreign Application Priority Data
Jun. 17, 2020 (KR) .................. 10-2020-0073847

(51) Int. Cl.
*A61L 31/08* (2006.01)
*A61L 31/16* (2006.01)
(52) U.S. Cl.
CPC ............. *A61L 31/088* (2013.01); *A61L 31/16* (2013.01); *A61L 2300/802* (2013.01); *A61L 2400/12* (2013.01); *A61L 2420/02* (2013.01)
(58) Field of Classification Search
CPC ................................ A61L 31/088; A61L 31/16
See application file for complete search history.

(56) References Cited

U.S. PATENT DOCUMENTS

2007/0160639 A1* 7/2007 Pantelidis ............... A61L 31/16
514/291
2008/0195192 A1 8/2008 Parsonage
2019/0046299 A1 2/2019 Kim

FOREIGN PATENT DOCUMENTS

KR 10-1064214 B1 9/2011
KR 10-1701264 B1 2/2017
KR 10-2019-0066369 A 6/2019

OTHER PUBLICATIONS

E1, Centrimonium Bromide, Jun. 29, 2024, Wikipedia, pp. 1-10 (Year: 2024).*
Wang et al., Fabrication of a Novel Polymer-Free Nanostructured Drug-Eluting Coating for Cardiovascular Stents, 2013, Applied Materials and Interfaces, 5,pp. 10337-10345 (Year: 2013).*

(Continued)

Primary Examiner — Dah-Wei D. Yuan
Assistant Examiner — Andrew J Bowman
(74) Attorney, Agent, or Firm — CANTOR COLBURN LLP

(57) ABSTRACT

Provided are a method of manufacturing a stent for drug release that may be coated with a drug by forming a 3D nanostructured film on the surface of a stent and a stent for drug release manufactured thereby, more particularly, a method of manufacturing a stent for drug release including: (a) preparing a stent, (b) forming a 3D nanostructured film on a surface of the stent; and (c) surface-treating the 3D nanostructured film, and a stent for drug release manufactured thereby.

15 Claims, 17 Drawing Sheets

(56) References Cited

OTHER PUBLICATIONS

Yao Wang et al., "Fabrication of a Novel Polymer-Free Nanostructured Drug-Eluting Coating for Cardiovascular Stents," ACS Applied Materials & Interfaces, Sep. 2013, pp. 10337-10345, American Chemical Society.
Seokyoung Yoon et al., "Synthesis of complex nanoparticles using bioceramic silica," CERAMIST, 2018, pp. 283-292, vol. 21, No. 3, English abstract.
Seong Kyu Song et al., "Spectroscopic Analysis of Silica Nanoparticles Modified with Silane Coupling Agent," Korean Chem. Eng. Res., Apr. 2011, pp. 181-186, vol. 49, No. 2, English abstract.
International Search Report mailed Sep. 27, 2021 for PCT/KR2021/006910.
Korean Office Action for KR Application No. 10-2020-0073847 mailed on Dec. 13, 2021. In conformance with MPEP 609—Concise explanation of the relevance includes issue date of KR OA and references cited therein.

\* cited by examiner

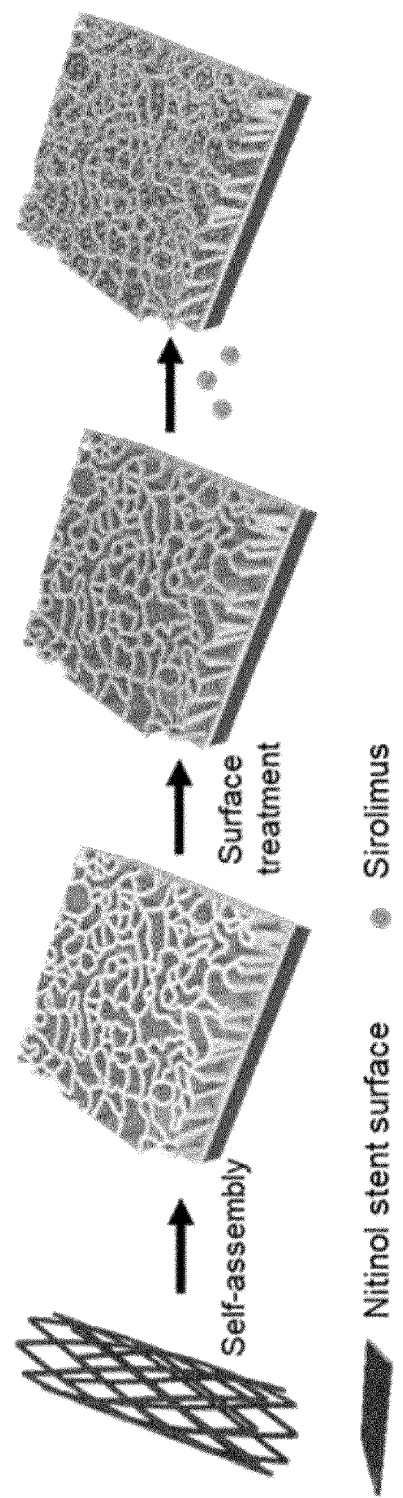

METHOD FOR MANUFACTURING STENT FOR DRUG RELEASE, INCLUDING FLEXIBLE NANOSTRUCTURED FILM CONNECTED IN THREE DIMENSIONS, AND STENT FOR DRUG RELEASE PREPARED THEREBY

CROSS-REFERENCE TO RELATED APPLICATION

This application claim the benefit of Korean Patent Application No. 10-2020-0073847, filed on Jun. 17, 2020, in the Korean Intellectual Property Office, the disclosure of which is incorporated herein in its entirety by reference.

BACKGROUND

1. Field

The present invention relates to a method of manufacturing a stent for drug release formed of various materials and including a flexible nanostructured film, which have various sizes and connected in three dimensions, on the surface of the stent and a stent for drug release prepared thereby.

2. Description of the Related Art

A stent, as a medical device for insertion into a human body, is inserted into a blood vessel narrowed by a blood clot or the like to assist blood to normally flow. With the increasing incidence of heart diseases in modern society due to various reasons such as changes in diet pattern and aging population, there has been increased demand for stents, and application fields thereof are expanded from the most common use for coronary artery diseases to nonvascular fields such as urethra, airways, esophagus, and internal organs in recent years.

In the early stage of development, a stent in the form of a balloon-tipped catheter was inserted into a blood vessel. However, since the stent cannot support walls of the blood vessel for a long period of time, the blood vessel walls are narrowed again causing recurrence of stenosis. Developed thereafter, a 'bare-metal stent', as a first-generation stent, is formed of a mesh-shaped metallic material and has an advantage of supporting the blood vessel walls for a long period of time. However, wounds made on the blood vessel walls during a procedure cause excessive proliferation of vascular smooth muscle cells, leading to recurrence of stenosis that results in blood vessel narrowing and thrombosis due to inflammation reaction.

In order to inhibit recurrence of stenosis, a second-generation stent loaded with a drug suppressing excessive proliferation of cells or formation of blood clots, i.e., 'drug-eluting stent (stent for drug release)' has been developed. By surface-treating the stent for loading the drug and then inserting the stent into the human body, narrowing of the blood vessel may be prevented. Mainly, a method of forming a nanostructure on the surface of a metal stent coated with a polymeric material and a method of forming a nanostructure on the surface of a metal stent etched using a laser have been used. However, the use of the polymeric material is disadvantages in that durability may deteriorate and the laser etching method is disadvantageous in that manufacturing costs are high and this method may affect physical properties of the stent. In addition, since methods of coating the surface of the stent with a nanostructure such as a nanowire and a nanoparticle are disadvantageous in that the coating is easily detached from the surface of the stent due to weak binding force between each nanostructure and the stent.

SUMMARY

The present invention has been proposed to solve various problems including the above problems, and an object of the present invention is to provide a method of manufacturing a stent for drug release in which a flexible nanostructured film with various sizes and connected in three dimensions is formed on the surface of a stent formed of various materials in a bottom-up method under chemically mild conditions and a stent for drug release manufactured thereby.

Additional aspects will be set forth in part in the description which follows and, in part, will be apparent from the description, or may be learned by practice of the presented embodiments.

An aspect of the present invention to achieve the above-described object provides a method of manufacturing a stent for drug release, the method including: (a) preparing a stent; (b) forming a three-dimensional (3D) nanostructured film on a surface of the stent; and (c) surface-treating the 3D nanostructured film.

In an embodiment of the present invention, the step (b) may include: (b1) adding an ionic surfactant and an auxiliary spacer to a reactor in which the stent is immersed, and stirring and heating a mixture; (b2) adding a ceramic precursor solution to the reactor, and stirring and heating the mixture; and (b3) removing residual substances by washing the stent.

In an embodiment of the present invention, the ionic surfactant may have a cation or an anion and the auxiliary spacer may have an ion opposite to that of the ionic surfactant.

In an embodiment of the present invention, in the step (b1), the ionic surfactant and the auxiliary spacer may be self-assembled to form a micelle structure on the surface of the stent.

In an embodiment of the present invention, in the step (b2), the ceramic precursor may be laminated on the surface of the stent.

In an embodiment of the present invention, the stent may be formed of at least one material selected from the group consisting of an alloy, a biodegradable polymer, and a nondegradable polymer.

In an embodiment of the present invention, the alloy may include at least one selected from the group consisting of stainless steel, a cobalt-chromium alloy, a nickel-titanium alloy, and a platinum-chromium alloy, the biodegradable polymer may include at least one selected from the group consisting of polylacticacid (PLA), polyglycolide (PGA), polycaprolactone (PCL), polyethyleneglycol (PEG), and polylactic-co-glycolicacid (PLGA), and the nondegradable polymer may include at least one selected from the group consisting of polytetrafluoroethylene (PTFE), polyvinylalcohol (PVA), polyurethane (PU), and polyethylene terephthalate (PET).

In an embodiment of the present invention, the ceramic precursor solution may be is a silica precursor solution or a metal oxide precursor solution.

In an embodiment of the present invention, the silica precursor solution may include at least one selected from the group consisting of tetraethyl orthosilicate (TEOS), tetrapropyl orthosilicate (TPOS), tetrabutyl orthosilicate (TBOS), tetramethyl orthosilicate (TMOS), tetramethoxyvinylsilane (TMVS), tetrakis(2-hydroxyethyl) orthosilicate (THEOS), and sodium metasilicate.

In an embodiment of the present invention, the step (b2) may be performed in a temperature range of 40° C. to 95° C.

In an embodiment of the present invention, the ionic surfactant may be a cationic surfactant including at least one selected from the group consisting of cetyltrimethylammonium chloride (CTAC), cetyltrimethylammonium bromide (CTAB), dodecyltrimethylammonium bromide (DTAB), and tetradecyltrimethylammonium bromide (TTAB) or an anionic surfactant of sodium dodecyl sulphate (SDS) or sodium dodecyl benzene sulfonate (SDBS).

In an embodiment of the present invention, when the cationic surfactant is used, the auxiliary spacer may include at least one selected from the group consisting of sodium salicylate, sodium benzoate, sodium cinnamate, salicylic add, benzoic add, cinnamic add, sodium methoxybenzoate, methoxybenzoic acid, sodium vinylbenzoate, vinylbenzoic acid, and sodium p-toluenesulfonate.

In an embodiment of the present invention, the step (c) may include: (c1) adding a surface treatment compound to the reactor in which the stent having the 3D nanostructured film is immersed, and stirring and heating a mixture; and (c2) removing residual substances by washing the stent.

In an embodiment of the present invention, the surface treatment compound may be a silane coupling agent.

In an embodiment of the present invention, the method may further include (d) coating a drug on the surface of the 3D nanostructured film after the step (c).

In an embodiment of the present invention, the coating may be performed by at least one method selected from the group consisting of dip coating, spin coating, ultrasonic spray coating, electrospray coating, and vapor deposition coating.

Another aspect of the present invention provides a stent for drug release including: a stent; and a three-dimensional (3D) nanostructured film formed on a surface of the stent, wherein at least one drug selected from the group consisting of sirolimus, everolimus, biolimus, zotarolimus, paclitaxel, gemcitabine, and heparin is coated on a surface of the 3D nanostructured film.

In an embodiment of the present invention, the stent for drug release may include: a vascular stent; and a 3D nanostructured film formed on a surface of the vascular stent.

In an embodiment of the present invention, the stent for drug release may include: a non-vascular stent; and a 3D nanostructured film formed on a surface of the non-vascular stent.

BRIEF DESCRIPTION OF THE DRAWINGS

These and/or other aspects will become apparent and more readily appreciated from the following description of the embodiments, taken in conjunction with the accompanying drawings in which:

FIG. 1 is a schematic diagram for describing a method of manufacturing a stent for drug release including a flexible nanostructured film connected in three dimensions according to an embodiment of the present invention;

FIG. 2A shows SEM images of a surface of a bare-metal stent and FIG. 28 shows SEM images of a surface of a stent on which a 3D nanostructured film is formed using sodium salicylate (NaSal);

DETAILED DESCRIPTION

Figure 2A:
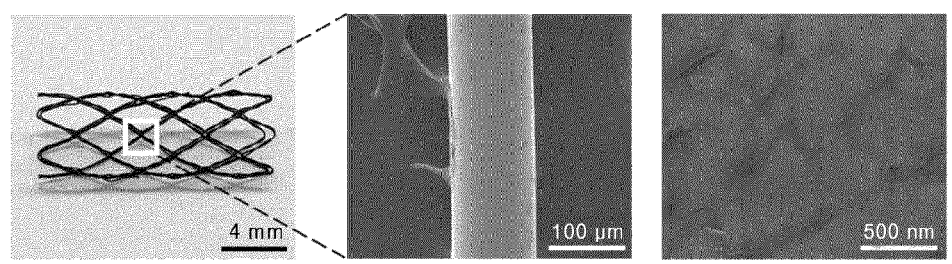

In the following detailed description, reference is made to the accompanying drawings that show, by way of illustration, specific embodiments in which the invention may be practiced. These embodiments are described in sufficient detail to enable those skilled in the art to practice the invention. It is to be understood that the various embodiments of the invention, although different, are not necessarily mutually exclusive. For example, a particular feature, structure, or characteristic described herein, in connection with one embodiment, may be implemented within other embodiments without departing from the spirit and scope of the invention. In addition, it is to be understood that the location or arrangement of individual elements within each disclosed embodiment may be modified without departing from the spirit and scope of the invention. The following detailed description is, therefore, not to be taken in a limiting sense, and the scope of the present invention is defined only by the appended claims, appropriately interpreted, along with the full range of equivalents to which the claims are entitled. In the drawings, like numerals refer to the same or similar functionality throughout the several views and length, area, and thickness in the drawings may be exaggerated for descriptive convenience.

Hereinafter, embodiments of the present invention will be described in detail with reference to the accompanying drawings so that these embodiments may be readily implemented by those skilled in the art.

FIG. 1 is a schematic diagram for describing a method of manufacturing a stent for drug release according to an embodiment of the present invention. According to the embodiment, the method of preparing a stent for drug release may include forming a flexible nanostructured film connected in three dimensions (3D nanostructured film) on the surface of a bare-metal stent and surface-treating the 3D nanostructured film for coating the film with a drug.

The forming of the 3D nanostructured film may include a micelle forming process to form micelles on the surface of the stent via self-assembly of an ionic surfactant and an auxiliary spacer having an ion opposite to that of the ionic surfactant by adding the ionic surfactant and the auxiliary spacer to a reactor in which a stent substrate is immersed in a predetermined ratio and stirring and heating the mixture, a ceramic precursor laminating process to laminate a ceramic precursor on the surface of the stent by adding a ceramic precursor solution to the reactor and stirring and heating the mixture after forming the micelles, and a washing process to remove residual substances and form the 3D nanostructured film by washing the stent after laminating the ceramic precursor.

Throughout the specification, the flexible nanostructured film connected in three dimensions refers to a thin film formed of nanostructures, wherein the nanostructures may be nanorods, nanoparticles, nanowires, nanoplates, nanocylinders, or nanocubes, and the nanostructures are integrally connected with each other in the form of a film coating the entire surface of the stent rather than fixed to the stent, A height of the connected nanostructures may be in the range of about 50 nm to about 3000 nm, but is not limited thereto.

The stent substrate may be formed of an alloy material such as stainless steel, a cobalt-chromium alloy, a nickel-titanium alloy, and a platinum-chromium alloy but is not limited thereto as long as the alloy material is used for the stent substrate. The stent substrate may be formed of a biodegradable polymer such as polyacticacid (PLA), polyglycolide (PGA), polycaprolactone (PCL), polyethyleneglycol (PEG), and polylactic-co-glycolicacid (PLGA), or a nondegradable polymer such as polytetrafluoroethylene (Tefron), polyvinylalcohol (PVA), polyurethane (PU), and polyethylenetelephthalate (PET) may be used.

The ceramic precursor solution may be a silica precursor solution or a precursor solution of an oxide of a metal such as titanium, aluminum, nickel, copper, iron, and cobalt. Among them, as the silica precursor solution, hydrolysable silane such as alkoxy silane, e.g., tetraethyl orthosilicate (TEOS), tetrapropyl orthosilicate (TPOS), tetrabutyl orthosilicate (TBOS), tetramethyl orthosilicate (TMOS), tetramethoxyvinylsilane (TMVS), tetrakis(2-hydroxyethyl) orthosilicate (THEOS), and sodium metasilicate may be used. The laminating of the ceramic precursor may be performed in a temperature range of 40 to 95° C.

The ionic surfactant may be a cationic surfactant such as cetyltrimethylammonium chloride (CTAC), cetyltrimethylammonium bromide (CTAB), dodecyltrimethylammonium bromide (©TAB), or tetradecyltrimethylammonium bromide (TTAB) or an anionic surfactant such as sodium dodecyl sulphate (SDS) or sodium dodecyl benzene sulfonate (SDBS). For formation of a 3D nanostructured film having large-sized pores, the cationic surfactant may preferably be used. When the cationic surfactant is used, the auxiliary spacer may be sodium salicylate, sodium benzoate, sodium cinnamate, salicylic acid, benzoic acid, cinnamic acid, sodium methoxybenzoate, methoxybenzoic acid, sodium vinylbenzoate, vinylbenzoic acid, or sodium p-toluenesulfonate, which have anionic properties opposite thereto.

In an embodiment of the present invention, the surface-treating for drug coating on the stent for drug release may include a process of stirring and heating a mixture of a material for surface treatment and the stent substrate including the 3D nanostructured film contained in the reactor and a washing process to form a surface-treated 3D nanostructured film by modifying the original Si—OH-containing hydrophilic surface by removing residual substances. The material for surface treatment may be a silane with an alkyl group such as a methyl group, a vinyl group, a phenyl group, an octyl group, a hexadecyl group, or an octadecyl group, e.g., octyltrimethoxysilane (OTMS), hexadecylytrimethoxysilane (HDTMS), octadecyltrimethoxysilane (ODTMS), and phenyltrimethoxysilane (PTMS). Alternatively, the surface treatment may be performed by a silane with a hydroxy group, an amine group, an aldehyde group, a carboxyl group, or a mercapto group, e.g., 3-aminopropyl triethoxysilane (APTES) and 3-mercaptopropyl trimethoxysilane (MPTMS).

In an embodiment of the present invention, the method of manufacturing a stent for drug release may further include coating a drug on the surface of the surface-treated 3D nanostructured film. The drug may be sirolimus, everolimus, biolimus, zotarolimus, paclitaxel, heparin, or the like, and a coating method may be dip coating, spin coating, ultrasonic spray coating, electrospray coating, vapor deposition coating, or the like.

According to another aspect of the present invention, provided is a stent for drug release including a stent and a 3D nanostructured film formed on the surface of the stent. The stent for drug release may be configured such that at least one drug selected from the group consisting of sirolimus, everolimus, biolimus, zotarolimus, paclitaxel, gemcitabine, and heparin is coated on the surface of the 3D nanostructured film.

In an embodiment of the present invention, the stent and the 3D nanostructured film may be alternately laminated, without being limited thereto.

In an embodiment, the 3D nanostructured film and the polymer layer may be coated alternately on the polymer stent. Also, the 3D nanostructured film and a metal layer may be coated alternately on the polymer stent. Also, the 3D nanostructured film and the metal layer or the polymer layer may be coated on the polymer stent in any, order.

The stent may be provided in a tubular form in which a plurality of wires are intersected to be inserted into a human body such as esophagus, biliary tract, ureter, prostatic duct, and blood vessel to widen an inner space thereof.

Vascular stents are classified into coronary artery stents used for cardiovascular stenosis, peripheral stents, and cerebral stents and tiny with a very small diameter of about 2 to 3 mm since stents are applied to blood vessels. Because a balloon catheter is inserted into the blood vessel to expand a vascular stent, most of the vascular stents may be formed of a strong metal such as stainless steel or formed by cutting a wire in the case of using a shape memory alloy.

Non-vascular stents are stents mainly used in non-vascular obstructive diseases occurring in ureter, bile duct, and bronchi caused by urinary diseases, cholangiocarcinoma, pancreatic cancer, and the like and normally have a diameter of to 2 cm. In a thin tube like an ear, a very thin tube with a diameter of several millimeters may be used. The non-vascular stent may be made by twisting a thin wire with hands.

According to an embodiment of the present invention, a stent for drug release to be inserted into a human body may be provided by forming a film, in which silica nanostructures are connected in three dimensions, on the surface of a vascular or non-vascular stent.

Hereinafter, the present invention will be described in more detail with reference to the following experimental examples. However, the following experimental examples are merely presented to exemplify the present invention, and the scope of the present invention is not limited thereto.

Example 1

First, a stent substrate was cleaned by sonication, washed with distilled water, and stored. The washed stent was added to a solution including triethanolamine (TEA), an ionic surfactant, and an auxiliary spacer and the mixture was stirred for 1 hour. A ceramic precursor solution was added thereto and the resultant was stirred and heated at 80° C. for 1 hour. After termination of the reaction, the stent was cleaned by sonication using ethanol and distilled water to form a 3D nanostructured silica film. In order to remove residual substances present in the stent on which the 3D nanostructured silica film was formed, the stent was cleaned by sonication for 1 hour with a mixed solution of methanol and hydrochloric acid (HCl). The cleaned stent was added to a reactor containing 100 mL of toluene and a predetermined amount of OTMS and the mixture was stirred and heated at 50° C. for 5 hours while injecting argon gas thereinto. After the reaction was terminated, the stent was washed with ethanol and distilled water, dried and stored at room temperature.

Example 2

Methylene blade dye was added to a 10 mM PBS buffer solution and dissolved by sonication for 1 hour to prepare a methylene blue solution with a concentration of 0.5 mg/mL. The stent having a size of 1 cm×1 cm prepared according to Example 1 above was added to a tube and 3 mL of the methylene blue solution was added thereto such that the stent was sufficiently dipped therein. Then, dip coating was performed at 500 rpm for 12 hours. The 3D nanostructured silica film coated with methylene blue was sufficiently washed with distilled water, followed by stirring at 500 rpm over 24 hours in a state of being sufficiently immersed in 3 mL of a 10 mM PBS buffer solution to release methylene blue. Then, a certain amount of a solution in which methylene blue was released was used to observe peaks at around 665 nm using a UV-Vis spectrometer.

Experimental Example 1

Figure 2B:
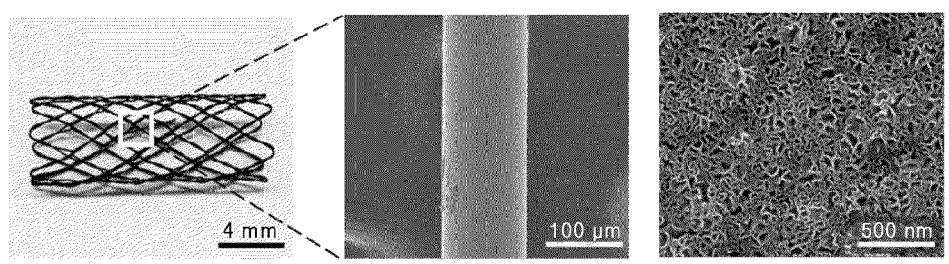
Figure 3:
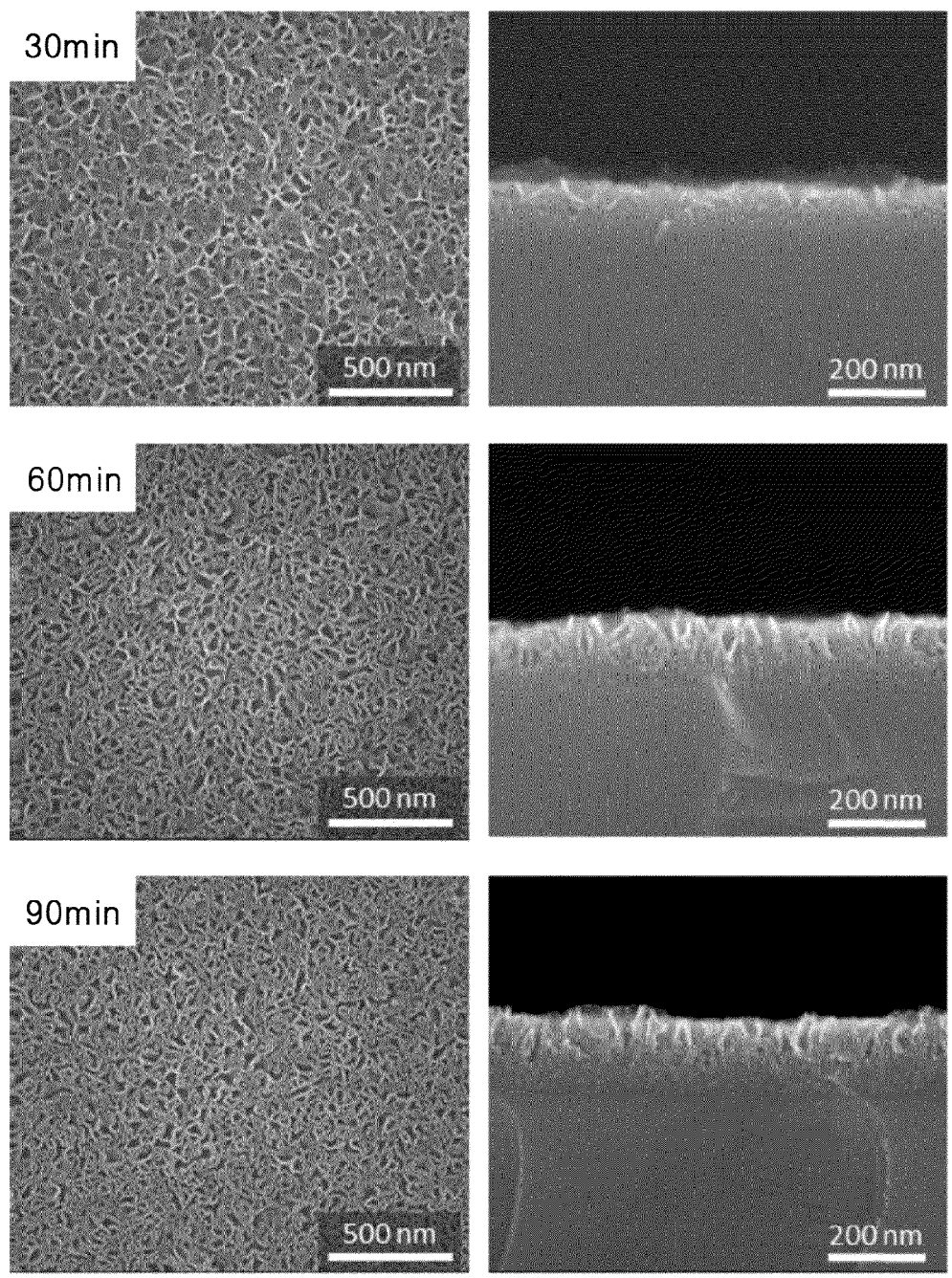
FIGS. 3 to 6 show SEM images of surfaces and cross-sections of 3D nanostructured films prepared using NaSal according to an embodiment of the present invention.
Figure 4:
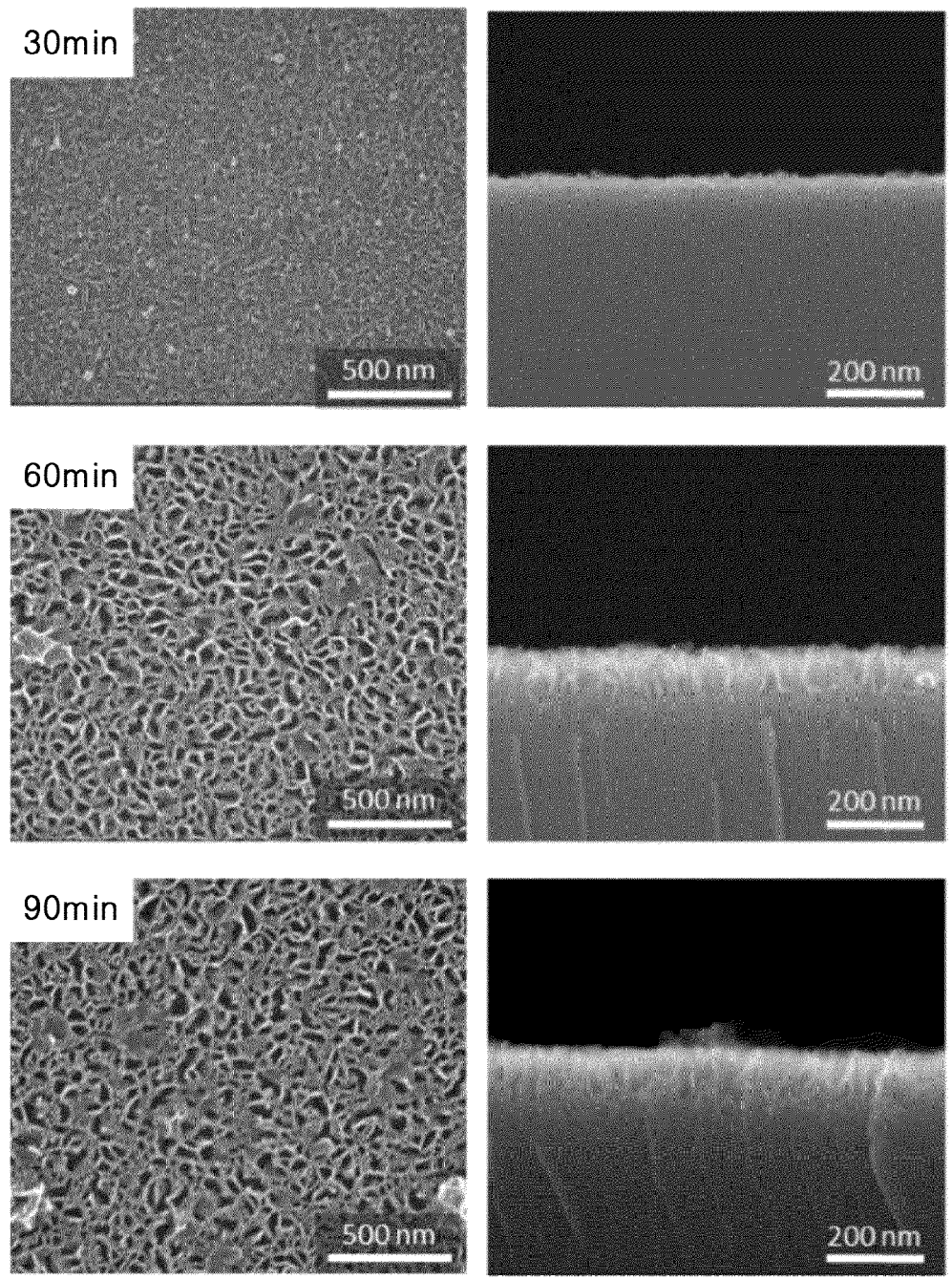
Figure 5:
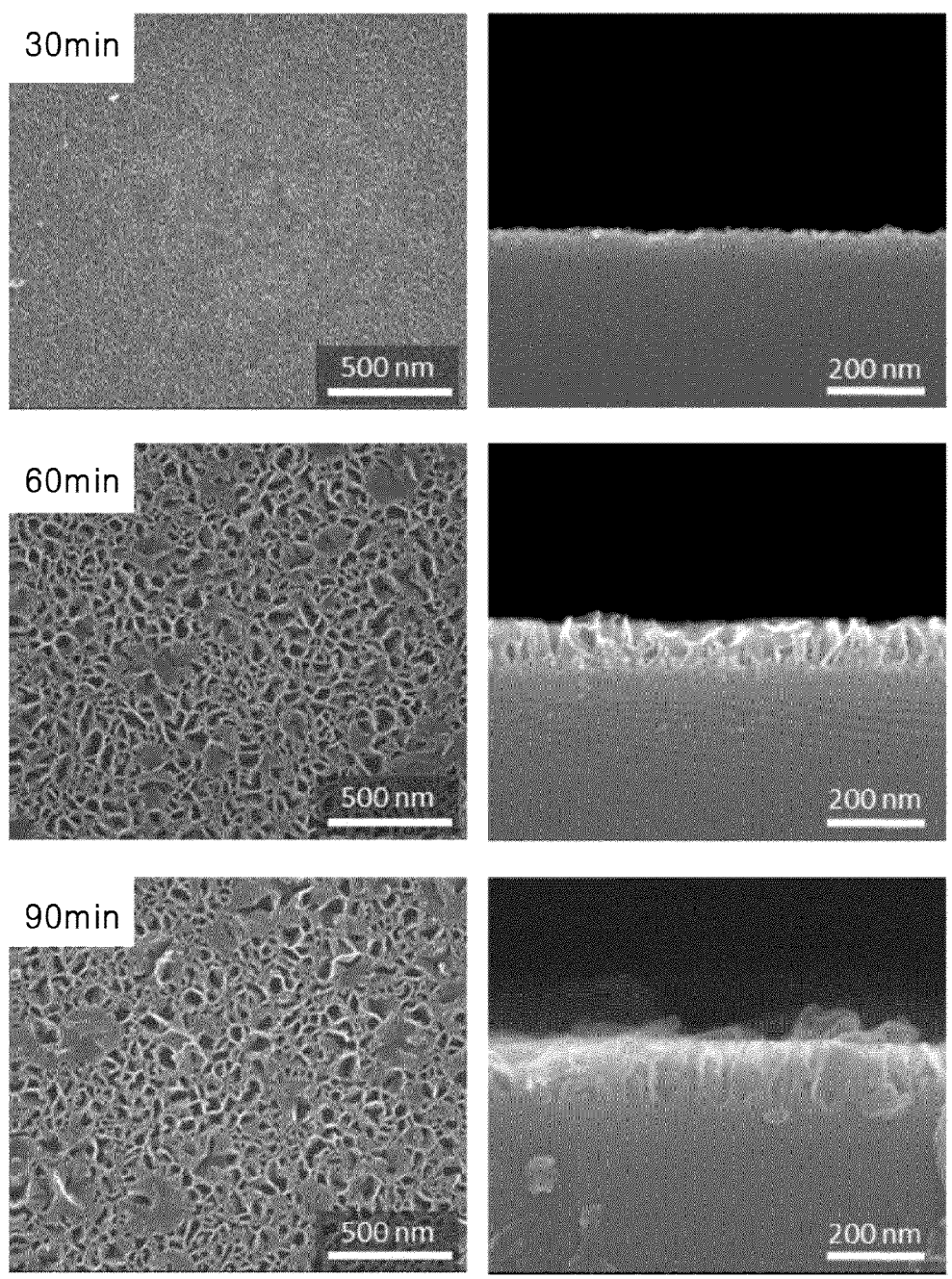
Figure 6:
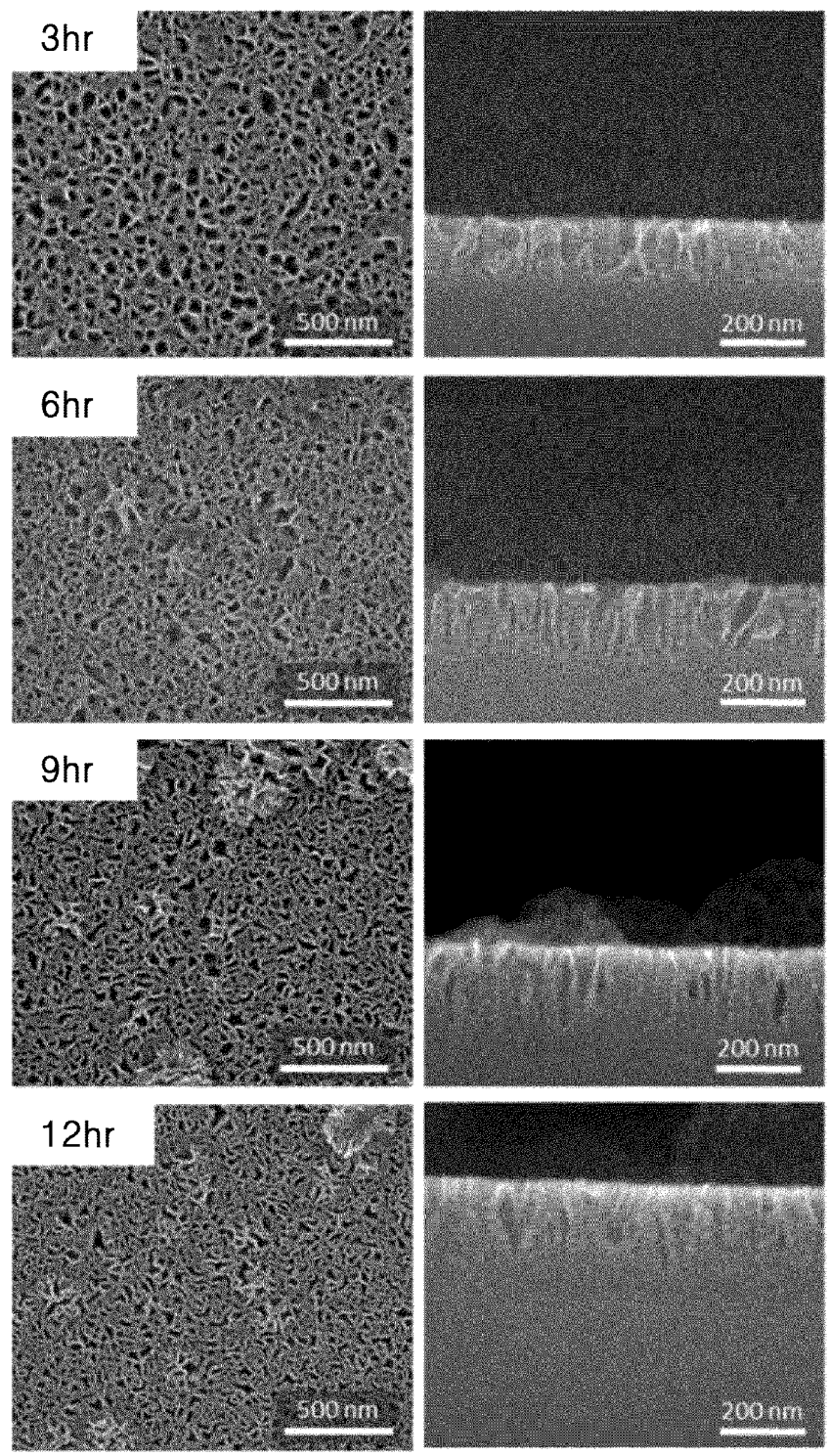

The structure of the 3D nanostructured silica film prepared in Example 1 was analyzed and results thereof are shown in FIGS. 2 to 9, FIG. 2A shows SEM images of a surface of a bare-metal stent and FIG. 2B shows SEM images of a surface of a stent prepared according to Example 1. Referring to FIG. 2A and FIG. 2B, it was confirmed that an ionic surfactant and an auxiliary spacer were self-assembled to form a film, in which silica nanostructures were connected in three dimensions, on the surface of the stent.

Figure 7:
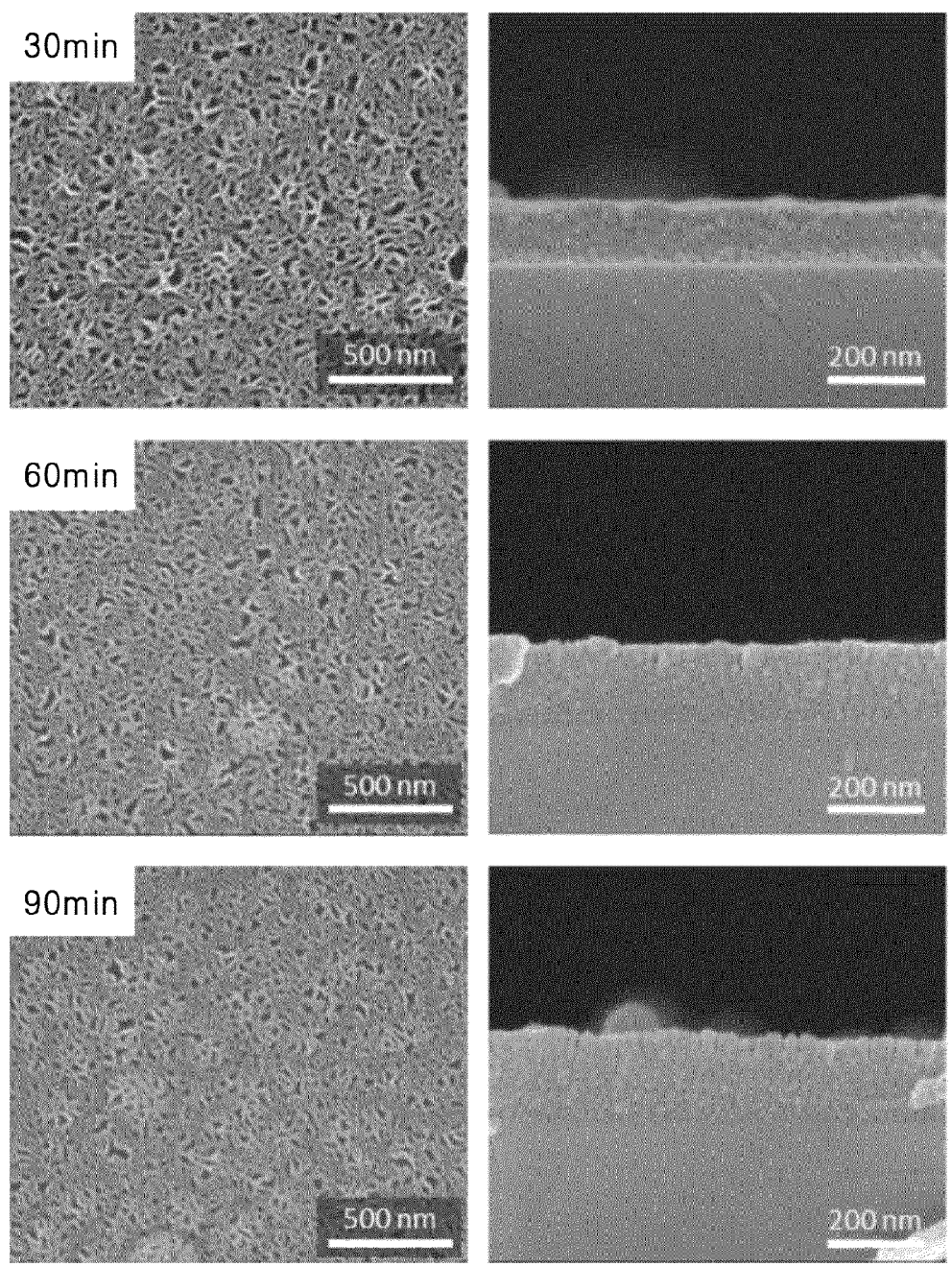
FIGS. 7 and 8 show SEM images of surfaces and cross-sections of 3D nanostructured films prepared using sodium benzoate (NaBen) according to an embodiment of the present invention.
Figure 8:
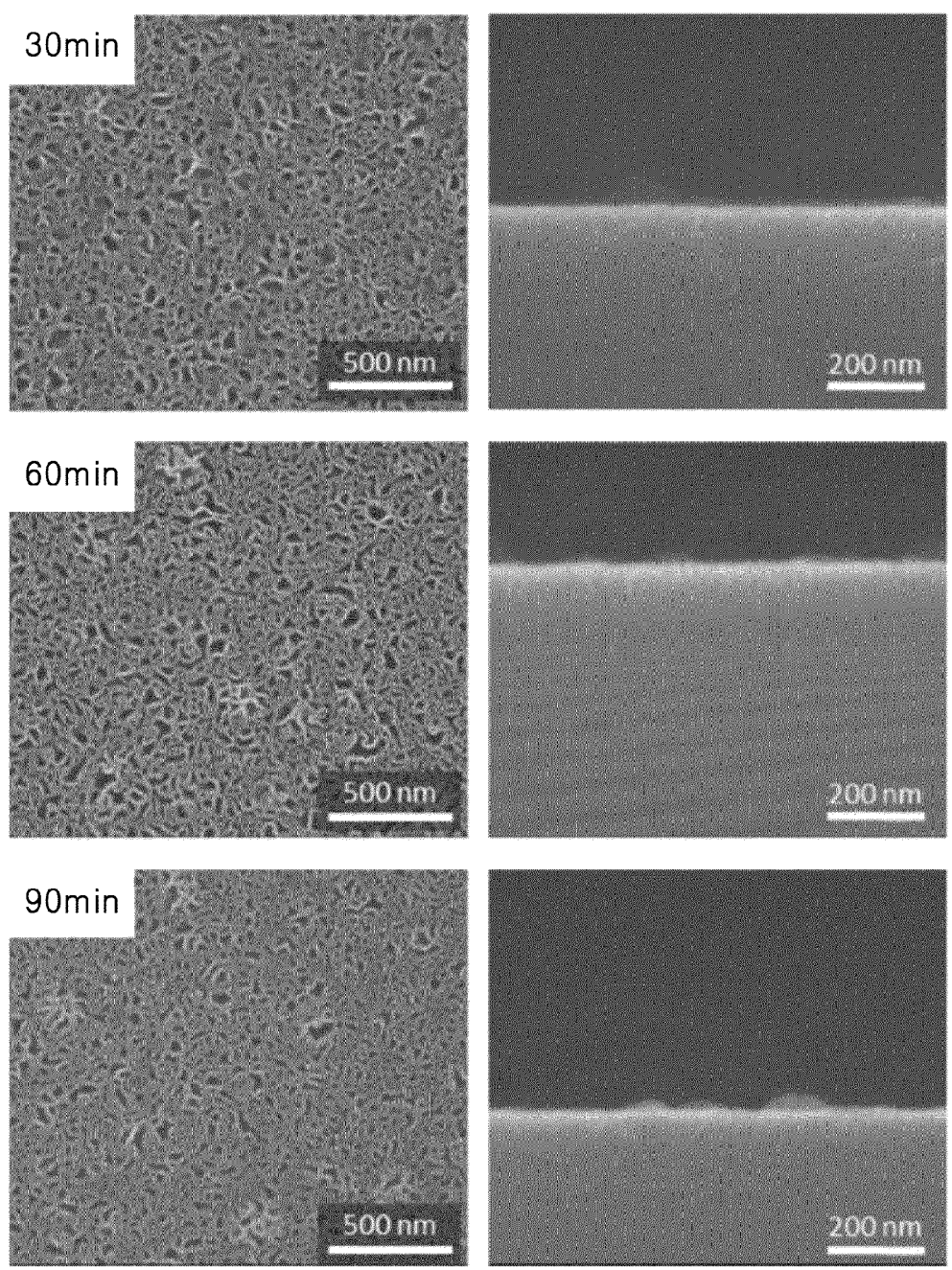
Figure 9:
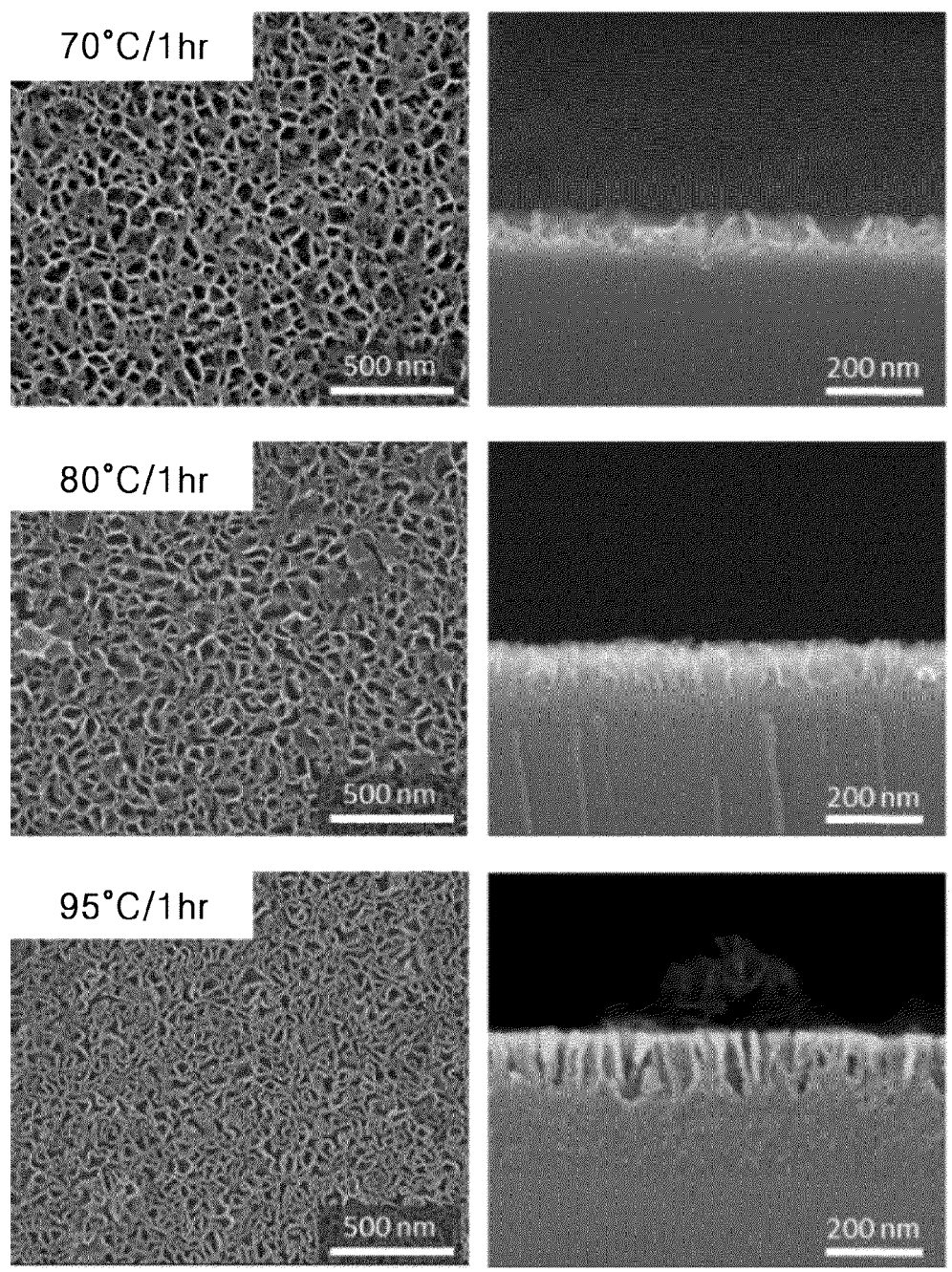
FIG. 9 shows SEM images of surfaces and cross-sections of a 3D nanostructured film prepared using NaSal according to an embodiment of the present invention.

FIGS. 3 to 6 show SEM images of surfaces and cross-sections of 3D nanostructured films over time prepared using NaSal, as the auxiliary spacer. FIGS. 3 to 6 shows cases in which concentration ratios of CTAC:NaSal were 1:0.85, 1:1.7, and 1:3.4, respectively and stirring was performed at 80° C. FIG. 7 shows SEM images of surfaces and cross-sections of a 3D nanostructured silica film when a concentration ratio of CTAC:NaSal was and stirring was performed at 70° C. FIGS. 7 and 8 show SEM images of surfaces and cross-sections of 3D nanostructured silica films prepared using NaBen as the auxiliary spacer when concentration ratios of CTAC:NaBen were 1:0.85 and 1:1.7 respectively. FIG. 9 shows SEM images of surfaces and cross-sections of a 3D nanostructured silica film when a concentration ratio of CTAC:NaSal was 1:1.7, with respect to temperature. Referring to FIGS. 3 to 9, it was confirmed that 3D nanostructured films having various pore sizes may be formed using the auxiliary spacer and pore size and thickness may be adjusted according to reaction temperature and time.

Experimental Example 2

Figure 10A:
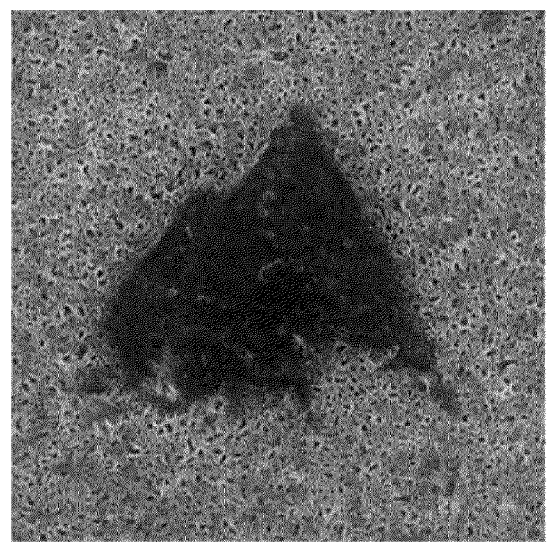
FIG. 10A to FIG. 10D show nano-indentation result values of a 3D nanostructured film formed on a 3D wafer according to an embodiment of the present invention.
Figure 10B:
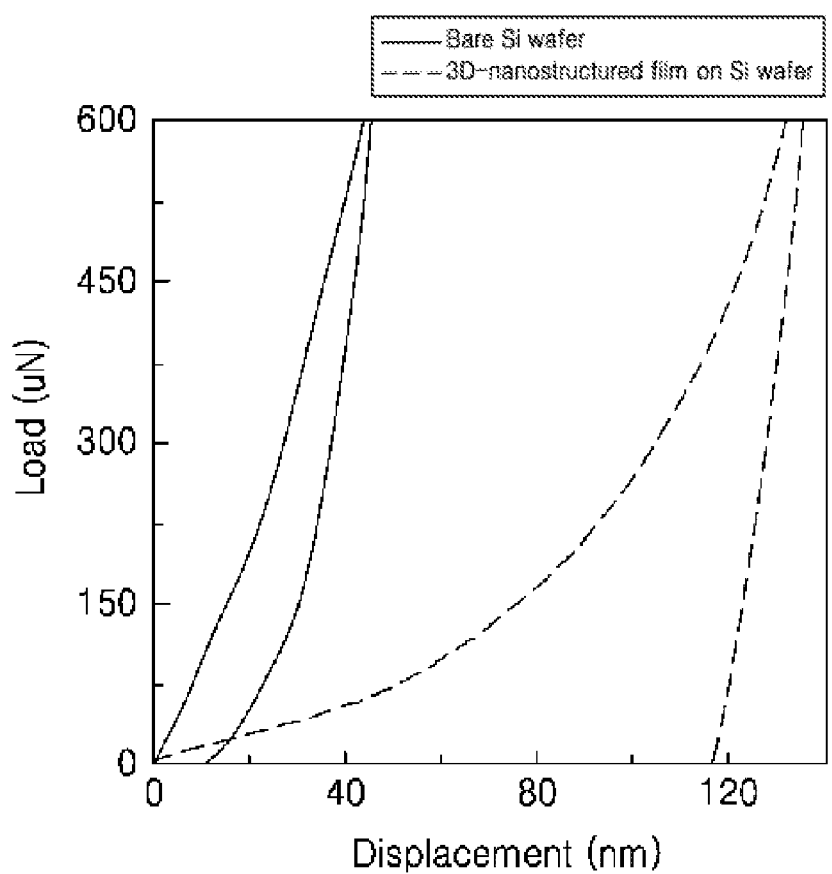
Figure 10C:
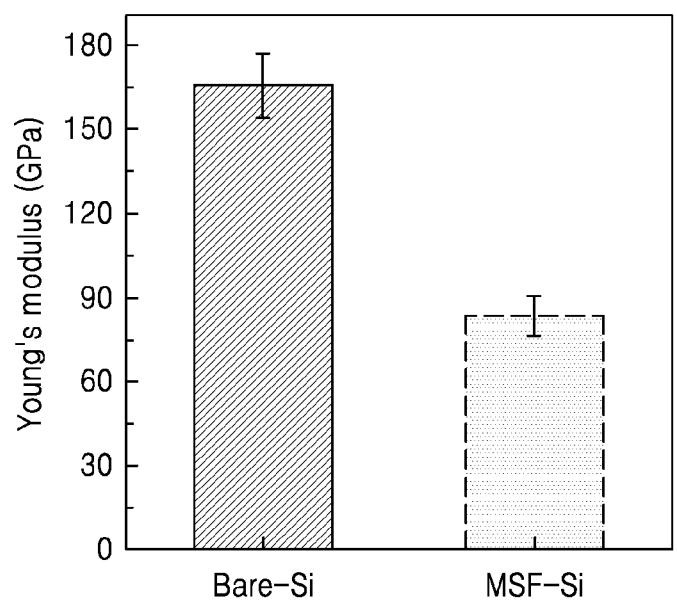
Figure 10D:
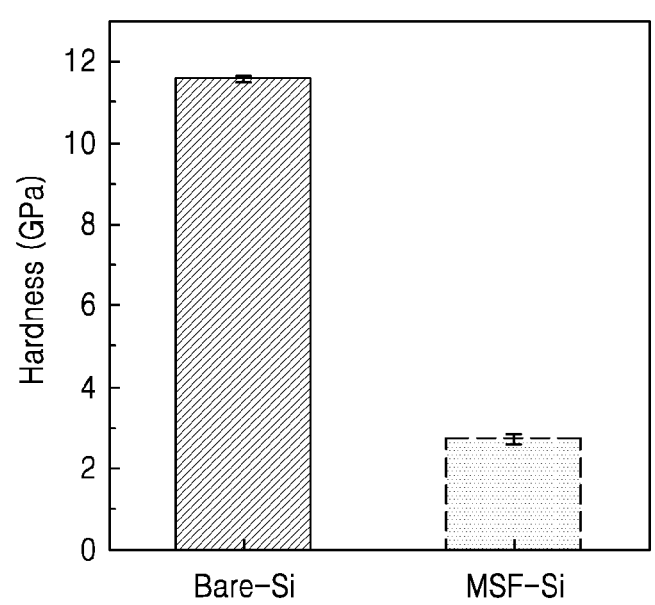

A bare Si substrate and the 3D nanostructured film prepared according to Example 1 were tested by a nano-indentation test and results are shown in FIG. 10A to FIG. 10D. In FIG. 10A to FIG. 10D, FIG. 10A shows a deformed wafer surface after the nano-indentation test, FIG. 10B shows a displacement pattern in indented depth with respect to load, FIG. 10C and FIG. 10D show Young's modulus and hardness measured by the nano-indentation test, Based thereon, it was confirmed that displacement increased at a maximum load and the Young's modulus and hardness decreased since the 3D nanostructured film was formed on the surface of the wafer. The difference of physical properties from those of conventional bulk silica is considered because nano-sized structures are connected with each other in three dimensions with space therebetween.

Experimental Example 3

Figure 11A:
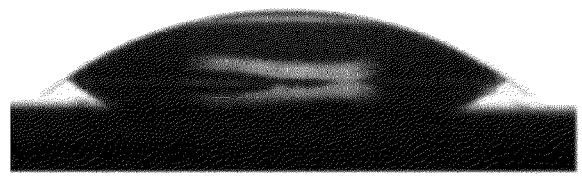
FIG. 11A to FIG. 11D show contact angles of wafers on which a 3D nanostructured film according to an embodiment of the present invention is formed and contact angles of wafers on which a 3D nanostructured film is formed and hydrophobically surface-treated.
Figure 11B:
Figure 11C:
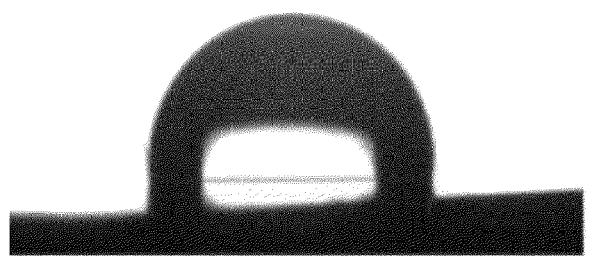
Figure 11D:
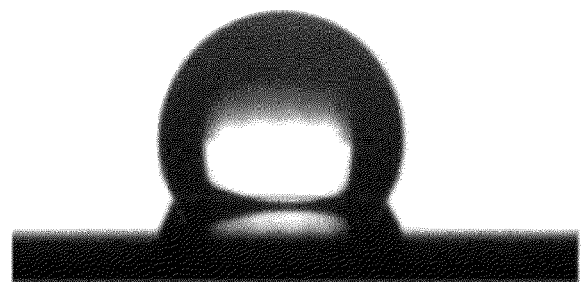
Figure 12A:
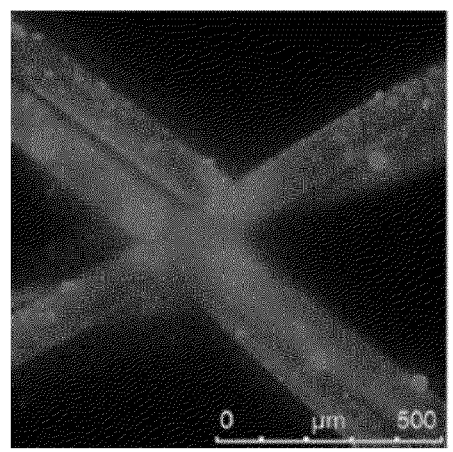
FIG. 12A to FIG. 12C show fluorescent images of stents surface-treated with APTES, OTMS, and ODTMS and loaded with fluorescein dye and vile red dye according to an embodiment of the present invention.
Figure 12B:
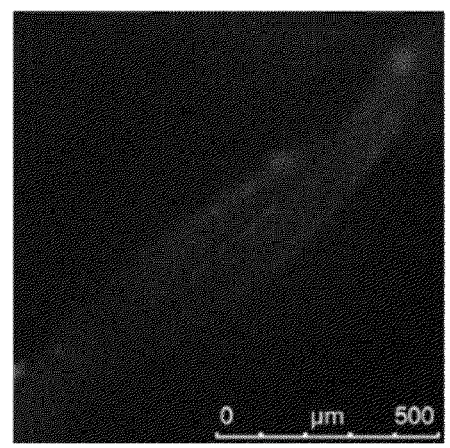
Figure 12C:
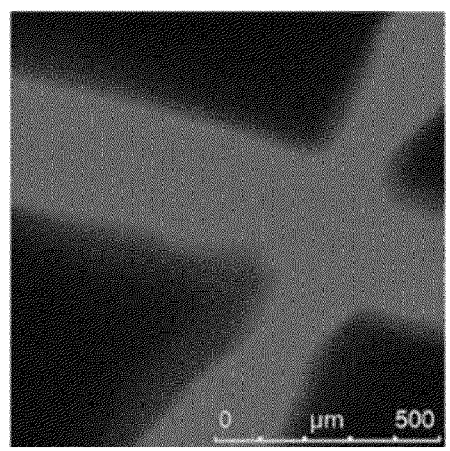

Contact angles of a bare Si substrate and the 3D nanostructured film prepared according to Example 1 were measured and results are shown in FIG. 11A to FIG. 11D. In FIG. 11A to FIG. 11D, FIG. 11A shows a contact angle of the bare Si wafer, FIG. 11B shows a contact angle of a wafer on which the 3D nanostructured film is formed, and FIG. 11C and FIG. 11D are contact angles of wafers on which the 3D nanostructured film is formed after hydrophobic surface treatment once and twice, respectively. FIG. 12A to FIG. 12C show fluorescent images of stents surface-treated with APTES, OTMS, and ODTMS and loaded with fluorescein dye and vile red dye according to an embodiment of the present invention. Based thereon, it was confirmed that the 3D nanostructured film may be surface-treated and contact angle increased by surface treatment.

Experimental Example 4

Figure 13:
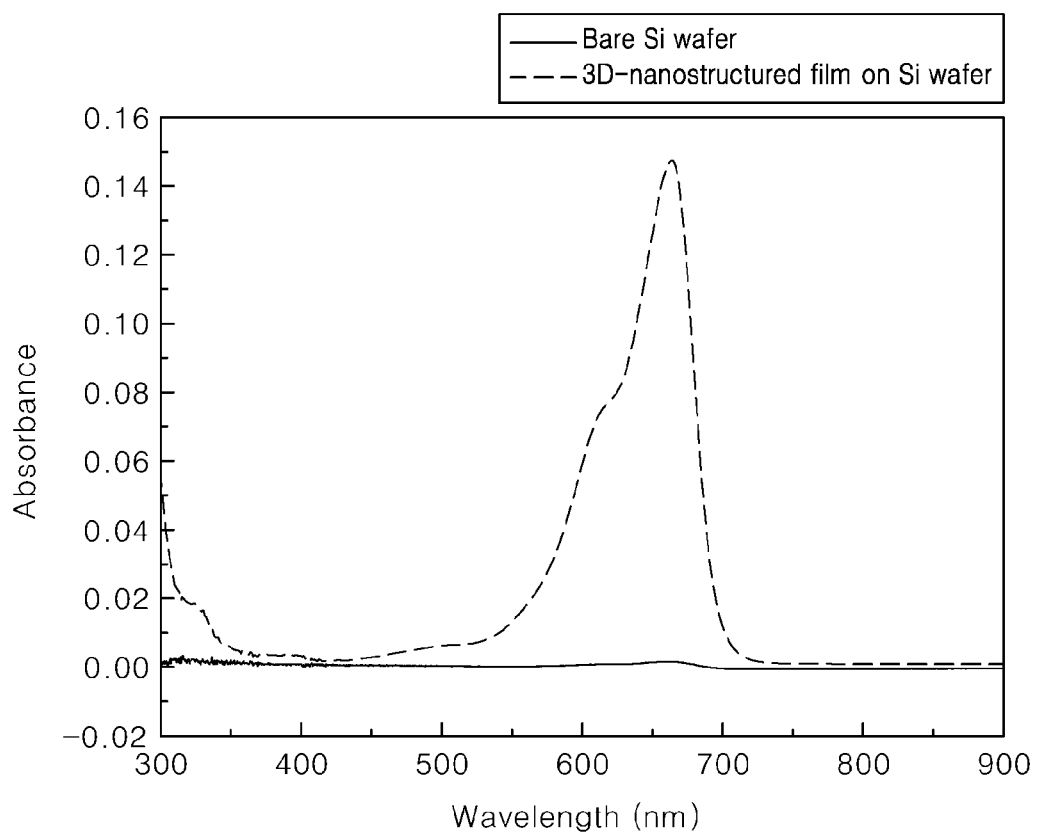
FIG. 13 shows spectroscopic analysis results illustrating elution degrees of a substance coated on a wafer on which a 3D nanostructured film is formed and hydrophobically surface-treated.

In order to identify drug-releasing function of the stent prepared according to an embodiment of the present invention, degrees of eluting a drug was observed after coating the drug. Referring to spectroscopic analysis results shown in FIG. 13, it can be seen that a stent for drug release may be prepared via the 3D nanostructured film.

According to the embodiments of the present invention as described above, flexible nanostructured film connected in three dimensions having various sizes may be formed on surfaces of stents formed of various materials by a bottom-up method using the ionic surfactant and the auxiliary spacer under chemically mild conditions.

What is claimed is:
1. A method of manufacturing a stent for drug release, the method comprising:
 (a) preparing a stent;
 (b) forming a three-dimensional (3D) nanostructured film on a surface of the stent, wherein step (b) comprises (b1) adding an ionic surfactant and an auxiliary spacer to a reactor in which the stent is immersed, and stirring and heating a mixture, (b2) adding a ceramic precursor solution to the reactor, and stirring and heating the mixture, and (b3) removing residual substances by washing the stent; and
 (c) surface-treating the 3D nanostructured film,
 wherein the ionic surfactant is a cationic surfactant or an anionic surfactant,
 wherein when the cationic surfactant is present, the auxiliary spacer comprises at least one selected from the group consisting of sodium salicylate, sodium benzoate, sodium cinnamate, salicylic acid, benzoic acid, cinnamic acid, sodium methoxybenzoate, methoxybenzoic acid, sodium vinylbenzoate, vinylbenzoic acid, and sodium p-toluenesulfonate.

2. The method of claim 1, wherein the auxiliary spacer has an ion opposite to that of the ionic surfactant.

3. The method of claim 1, wherein in the step (b1),
the ionic surfactant and the auxiliary spacer are self-assembled to form a micelle structure on the surface of the stent.

4. The method of claim 1, wherein in the step (b2),
the ceramic precursor is laminated on the surface of the stent.

5. The method of claim 1, wherein the stent is formed of at least one material selected from the group consisting of an alloy, a biodegradable polymer, and a nondegradable polymer.

6. The method of claim 5, wherein the alloy comprises at least one selected from the group consisting of stainless steel, a cobalt-chromium alloy, a nickel-titanium alloy, and a platinum-chromium alloy, the biodegradable polymer comprises at least one selected from the group consisting of polylacticacid (PLA), polyglycolide (PGA), polycaprolactone (PCL), polyethyleneglycol (PEG), and polylactic-co-glycolicacid (PLGA), and the nondegradable polymer comprises at least one selected from the group consisting of polytetrafluoroethylene (PTFE), polyvinylalcohol (PVA), polyurethane (PU), and polyethylene terephthalate (PET).

7. The method of claim 1, wherein the ceramic precursor solution is a silica precursor solution or a metal oxide precursor solution.

8. The method of claim 7, wherein the silica precursor solution comprises at least one selected from the group consisting of tetraethyl orthosilicate (TEOS), tetrapropyl orthosilicate (TPOS), tetrabutyl orthosilicate (TBOS), tetramethyl orthosilicate (TMOS), tetramethoxyvinylsilane (TMVS), tetrakis(2-hydroxyethyl) orthosilicate (THEOS), and sodium metasilicate.

9. The method of claim 1, wherein the step (b2) is performed in a temperature range of 40° C. to 95° C.

10. The method of claim 1, wherein the cationic surfactant comprises at least one selected from the group consisting of cetyltrimethylammonium chloride (CTAC), cetyltrimethylammonium bromide (CTAB), dodecyltrimethylammonium bromide (DTAB), and tetradecyltrimethylammonium bromide (TTAB).

11. The method of claim 1, wherein the step (c) comprises:
(c1) adding a surface treatment compound to the reactor in which the stent having the 3D nanostructured film is immersed, and stirring and heating a mixture; and
(c2) removing residual substances by washing the stent.

12. The method of claim 11, wherein the surface treatment compound is a silane coupling agent.

13. The method of claim 1, further comprising (d) coating a drug on the surface of the 3D nanostructured film after the step (c).

14. The method of claim 13, wherein the coating is performed by at least one method selected from the group consisting of dip coating, spin coating, ultrasonic spray coating, electrospray coating, and vapor deposition coating.

15. The method of claim 1, wherein the anionic surfactant comprises sodium dodecyl sulphate (SDS) or sodium dodecyl benzene sulfonate (SDBS).

* * * * *